US006955666B2

(12) United States Patent
Edens et al.

(10) Patent No.: US 6,955,666 B2
(45) Date of Patent: Oct. 18, 2005

(54) LABIAL PAD HAVING A TAB

(75) Inventors: Ronald L. Edens, Cumming, GA (US); James J. Hlaban, Neenah, WI (US); Laura J Keely, Neenah, WI (US); Thomas P. Keenan, Appleton, WI (US); Sylvia B. Little, Marietta, GA (US); Mary L. McDaniel, Appleton, WI (US); Stephen L. Nunn, Appleton, WI (US); William G. Reeves, Appleton, WI (US); Heather A. Sorebo, Appleton, WI (US); Susan M. Weyenberg, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/038,970

(22) Filed: Dec. 31, 2001

(65) Prior Publication Data

US 2002/0193772 A1 Dec. 19, 2002

Related U.S. Application Data

(60) Provisional application No. 60/297,001, filed on Jun. 8, 2001.

(51) Int. Cl.$^7$ ................................................ A61F 13/15
(52) U.S. Cl. ............................ 604/385.04; 604/385.17
(58) Field of Search ....................... 604/385.17, 385.04

(56) References Cited

U.S. PATENT DOCUMENTS

| 1,941,717 | A | 1/1934 | Rabell |
| 3,738,362 | A | 6/1973 | Sneider |
| 3,780,730 | A | 12/1973 | Weisman |
| 4,898,642 | A | 2/1990 | Moore et al. |
| 5,591,150 | A | 1/1997 | Olsen et al. |
| 5,607,414 | A | 3/1997 | Richards et al. |
| 6,409,714 | B2 | 6/2002 | Osborn, III et al. |
| D483,483 | S | 12/2003 | Woon |
| 2003/0208178 | A1 | 11/2003 | Edens et al. |

*Primary Examiner*—Larry I. Schwartz
*Assistant Examiner*—C. Lynne Anderson
(74) *Attorney, Agent, or Firm*—Paul Yee

(57) ABSTRACT

An absorbent article (40) such as a labial pad configured for disposition within the vestibule (42) of a female wearer. The labial pad may be worn by females for catamenial purposes, incontinence protection, or both, and has at least one tab (94) extending outward from the periphery thereof.

33 Claims, 12 Drawing Sheets

LABIAL PAD HAVING A TAB

This application claims priority from U.S. Provisional Application No. 60/297001, filed Jun. 8, 2001.

BACKGROUND

The present invention relates generally to absorbent articles such as labial pads configured for disposition within the vestibule of a female wearer. More particularly, the present invention relates to labial pads having at least one tab extending outward from the periphery thereof.

A broad manner and wide variety of absorbent articles configured for the absorption of bodily exudates such as menstrual fluid are, of course, well known. With respect to feminine hygiene, the art has offered two basic types of feminine hygiene protection: sanitary napkins, developed for external wear about the pudendal region, and tampons, developed for residence within the vaginal cavity and interruption of menstrual flow therefrom. Hybrid feminine hygiene protection devices, attempting to merge the structural features of both within a single type of device, have also been proposed, but have not seen a meaningful measure of acceptance insofar as the effort to appropriate advantages has been overshadowed by the more demonstrable perpetuation of structural and anatomically functional disadvantages. Other less intrusive devices, known as labial or interlabial devices and characterized as having a portion which at least partially resides external of the wearer's vestibule, have also been proposed.

Many of these prior devices have not fully satisfied the demand of consumers for even smaller devices that may be worn interlabially by female wearers. In response thereto, several manufacturers have produced labial pads that are quite small in size in comparison to the prior devices described above. However, the construction of many of these devices appears to fail to recognize the wide range of variation that exists among women with regard to the location of their vaginal and urethral orifices. For example, some current devices often locate a significant portion of the absorbent core in the center of the device with a much less significant portion of the absorbent core located in the ends. Such devices afford less protection for the broad spectrum of women whose vaginal and urethral orifices are not located in the center of their vestibules. Other devices appear to provide a uniform distribution of absorbent core substantially throughout the longitudinal length of the device. However, the designs of many of these other devices typically fail to significantly enhance individualized fit and/or absorbent capacity.

Another factor affecting consumer acceptance is the ease of use, including disposition of the labial pad into proper placement and/or removal of the labial pad. Typically, the wearer grasps the labial pad with her fingers and disposes it into a desired placement within her vestibule. The wearer may also need to grasp the labial pad for removal, particularly if it is not expelled during urination. The disposition and/or removal of conventional labial pads is often accompanied with a great deal of difficulty. Thus, a need exists for an improved means which will facilitate sanitary disposition of a labial pad into an appropriate position within the vestibule as well as sanitary removal of a labial pad from the vestibule.

SUMMARY

The present inventors have recognized the deficiencies and problems inherent in the prior art and in response thereto conducted intensive research in developing innovative labial pads. While conducting their research, the inventors also discovered that at least one tab extending outward from the periphery of at least one transverse end area of a labial pad enhanced the ability of a wearer to sanitarily and easily dispose a labial pad within the vestibule and/or sanitarily and easily remove a labial pad from the vestibule.

In one embodiment of the present invention, an absorbent article is disclosed as having a fluid permeable cover, a liquid impermeable baffle and an absorbent. The absorbent is desirably situated between the cover and the baffle. The absorbent article is configured for disposition within the vestibule of a female wearer. The absorbent article includes a principal longitudinal axis, a principal transverse axis, a body-facing surface and a surface opposed to the body-facing surface. The absorbent article has a length, a width, a thickness, first and second spaced apart longitudinal sides and first and second spaced apart transverse end areas. The longitudinal sides extending between the transverse end areas and collectively defining the periphery of the absorbent article. Extending outward from the periphery of at least one transverse end area of the absorbent article is at least one tab.

In another embodiment of the present invention, an absorbent article is disclosed as including a liquid impermeable baffle and an absorbent. The absorbent article is configured for disposition within the vestibule of a female wearer. The absorbent article has a principal longitudinal axis, a principal transverse axis, a body-facing surface and a surface opposed to the body-facing surface. The absorbent article has a length, a width, a thickness, first and second spaced apart longitudinal sides and first and second spaced apart transverse end areas. The longitudinal sides extending between the transverse end areas and collectively defining the periphery of the absorbent article. Extending outward from the periphery of at least one transverse end area is at least one tab.

In still another embodiment, an absorbent article is disclosed as having an absorbent. The absorbent article is configured for disposition within the vestibule of a female wearer. The absorbent article includes a principal longitudinal axis, a principal transverse axis, a body-facing surface and a surface opposed to the body-facing surface. The absorbent article has a length, a width, a thickness, first and second spaced apart longitudinal sides and first and second spaced apart transverse end areas. The longitudinal sides extending between the transverse end areas and collectively defining the periphery of the absorbent article. Extending outward from the periphery of at least one transverse end area of the absorbent article is at least one tab.

DRAWINGS

The foregoing and other features, aspects and advantages of the present invention will become better understood with regard to the following description, appended claims and accompanying drawings where:

DESCRIPTION

Figure 1:
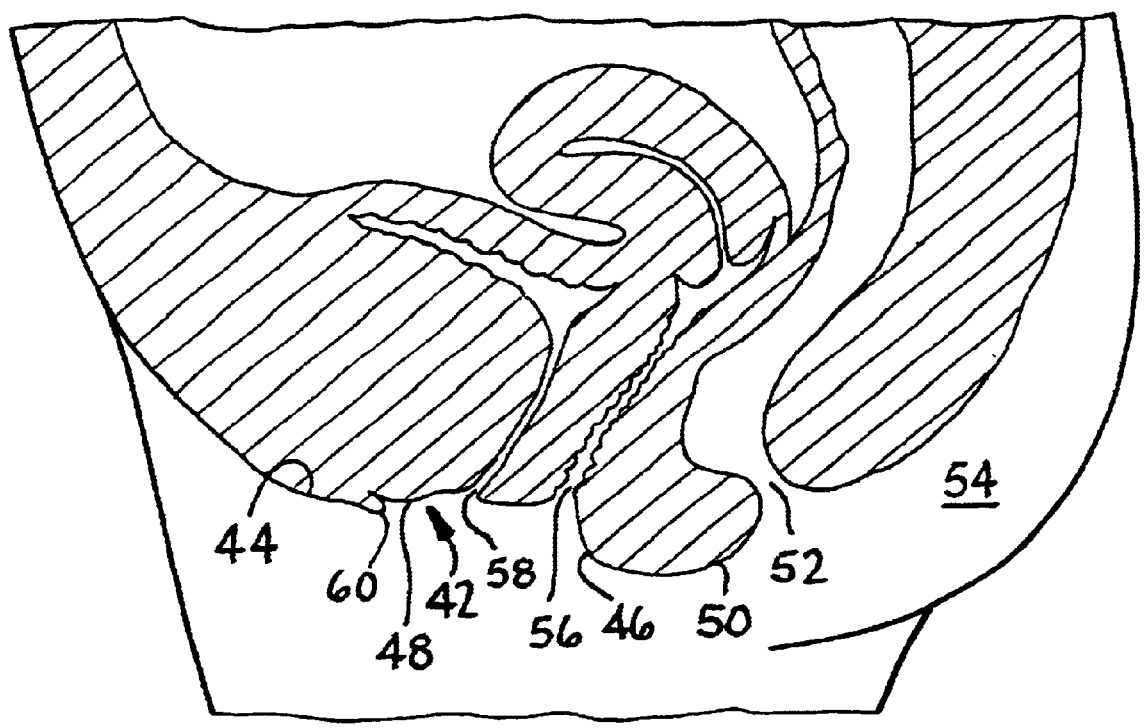
FIG. 1 is a simplified anatomical cross-sectional view of a human female illustrating the environment for an absorbent article such as a labial pad.
Figure 2:
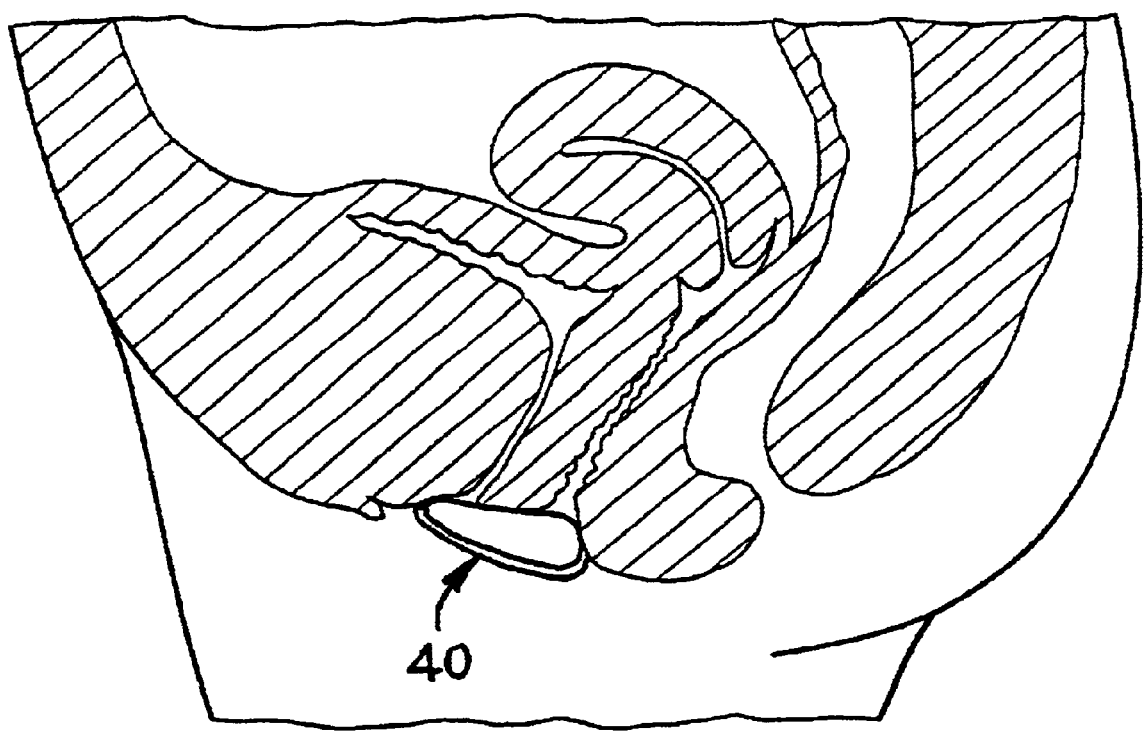
FIG. 2 is a simplified anatomical cross-sectional view of a human female illustrating an absorbent article, such as a labial pad, disposed within the vestibule of a wearer.

Turning to the figures of drawing, i.e., FIGS. 1 through 19, in each of which similar parts are identified with like reference characters, FIG. 2 illustrates diagrammatically an absorbent article, such as a labial pad, designated generally as 40, disposed within the vestibule of a wearer, designated generally as 42 (see also FIG. 1). As used herein, the term "labial pad" refers to a device having at least some absorbent components, and which is specifically configured for disposition in between the labia majora, extending at least partially into the vestibule (42) of a female wearer during use. For purposes of the ensuing description, the vestibule (42) is considered to be the region defined within the labia (not specifically shown in the figures herein) beginning at about a point lying caudally from the anterior labial commissure (44), extending rearward to the posterior labial commissure (46) and bounded inwardly by the floor (48) of the vestibule. One of skill in the art fully understands that there is a wide range of variation among women with respect to the relative size and shape of labia majora and labia minora as the same interrelatedly define the contour of the vestibule (42). For purposes of the present description, however, such differences will not specifically be addressed, it being recognized that in any event the disposition of the absorbent article (40) into the vestibule (42) will necessitate placement between the labia majora regardless of any such consideration respecting the labia minora. Lying caudally of the vestibule (42) is the perineum (50) which leads to the anus (52) in the region of the buttocks (54). Within the vestibule (42) itself is located the principal urogenital members which, for purposes pertinent here, are constituted of the vaginal orifice (56), the urethral orifice (58), and the clitoris (60). Given the foregoing simplified review of this anatomical region, and to facilitate the present description, the vestibule (42) will be considered generally to be the region between the posterior labial commissure (46) and the clitoris (60), for convenience. For a more comprehensive description of this portion of the human female anatomy, however, attention is invited to *Anatomy of the Human Body* by Henry Gray, Thirtieth American Edition (Carmine D. Clemente ed., Lea & Febiger, 1985) at 1571–1581.

As can be seen with reference to the anatomical structure illustrated in FIGS. 1 and 2, the absorbent article (40) is disposed at least partially within the vestibule (42) for at least partially occluding the same respecting fluid flow therefrom. In this regard, the predominant use of the absorbent article (40) is for the absorption of menstrual fluid emitted via the vaginal orifice (56); although the absorbent article is equally well adapted to serve as a type of incontinence device for absorption of urine as occurs upon minor, female incontinence.

Figure 3:
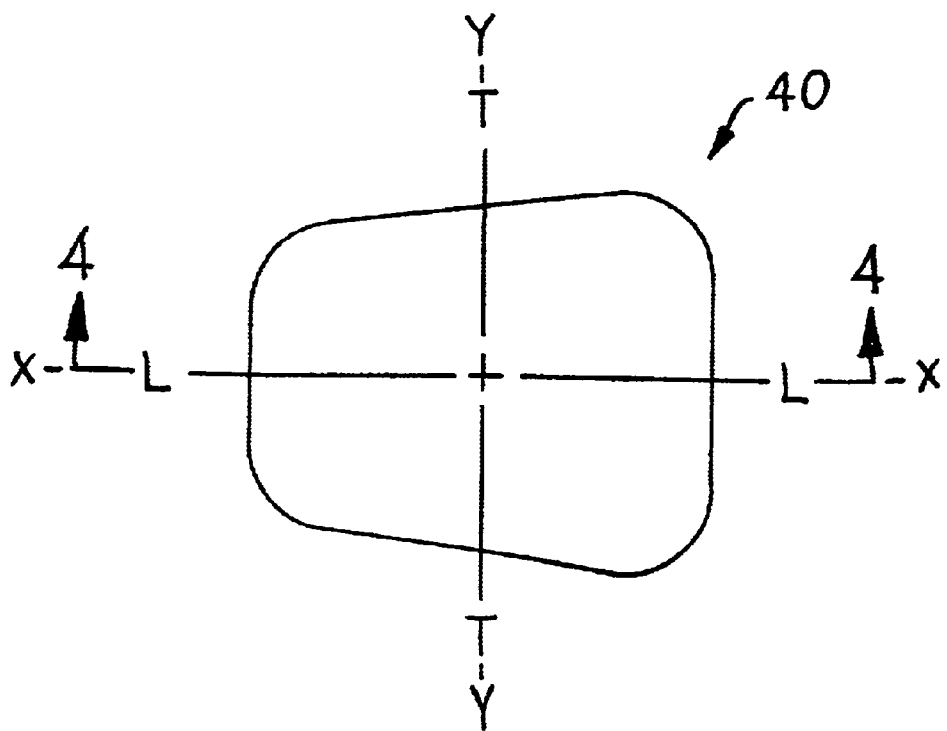
FIG. 3 is a top view illustrating a version of an absorbent article.
Figure 4:
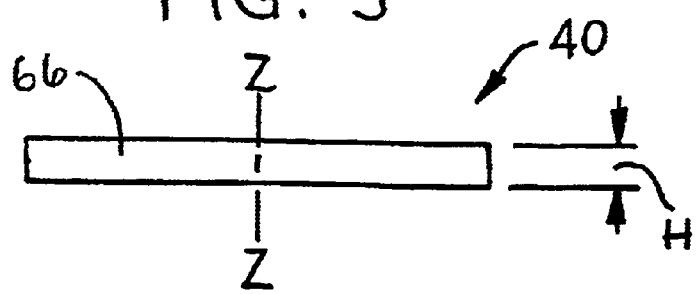
FIG. 4 is cross-sectional view of the absorbent article illustrated in FIG. 3 taken along line 4—4 thereof.

The absorbent article (40), a version of which is illustrated in FIG. 3, has a principal longitudinal axis (L) which generally runs along the x direction. As used herein, the term "longitudinal" refers to a line, axis or direction in the plane of the absorbent article (40) that is generally aligned with (e.g., approximately parallel to) a vertical plane that bisects a standing female wearer into left and right body halves when the absorbent article is in use. The longitudinal direction is generally illustrated in FIG. 3 by the x-axis. The absorbent article (40) also has a principal transverse axis (T). The terms "transverse," "lateral" or "y direction" as used herein generally refer to a line, axis or direction that is generally perpendicular to the longitudinal direction. The lateral direction is generally illustrated in FIG. 3 by the y-axis. The "z direction" is typically a line, axis or direction generally parallel to the vertical plane described above. The z direction is generally illustrated in FIG. 4 by the z-axis. The term "upper" refers generally to an orientation directed toward the wearer's head, while the terms "lower" or "downwardly" refer generally to an orientation directed toward the wearer's feet. For purposes of discussion herein, each layer of the absorbent article (40), e.g., a fluid permeable cover (62), a liquid impermeable baffle (64) and/or an absorbent (66), has an upper or body-facing surface and a lower surface also described as the surface opposed to the upper or body-facing surface.

Figure 5:
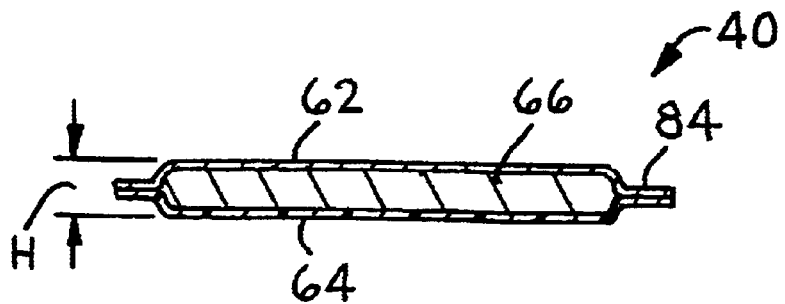
FIG. 5 is a cross-sectional view illustrating another version of an absorbent article.
Figure 6:
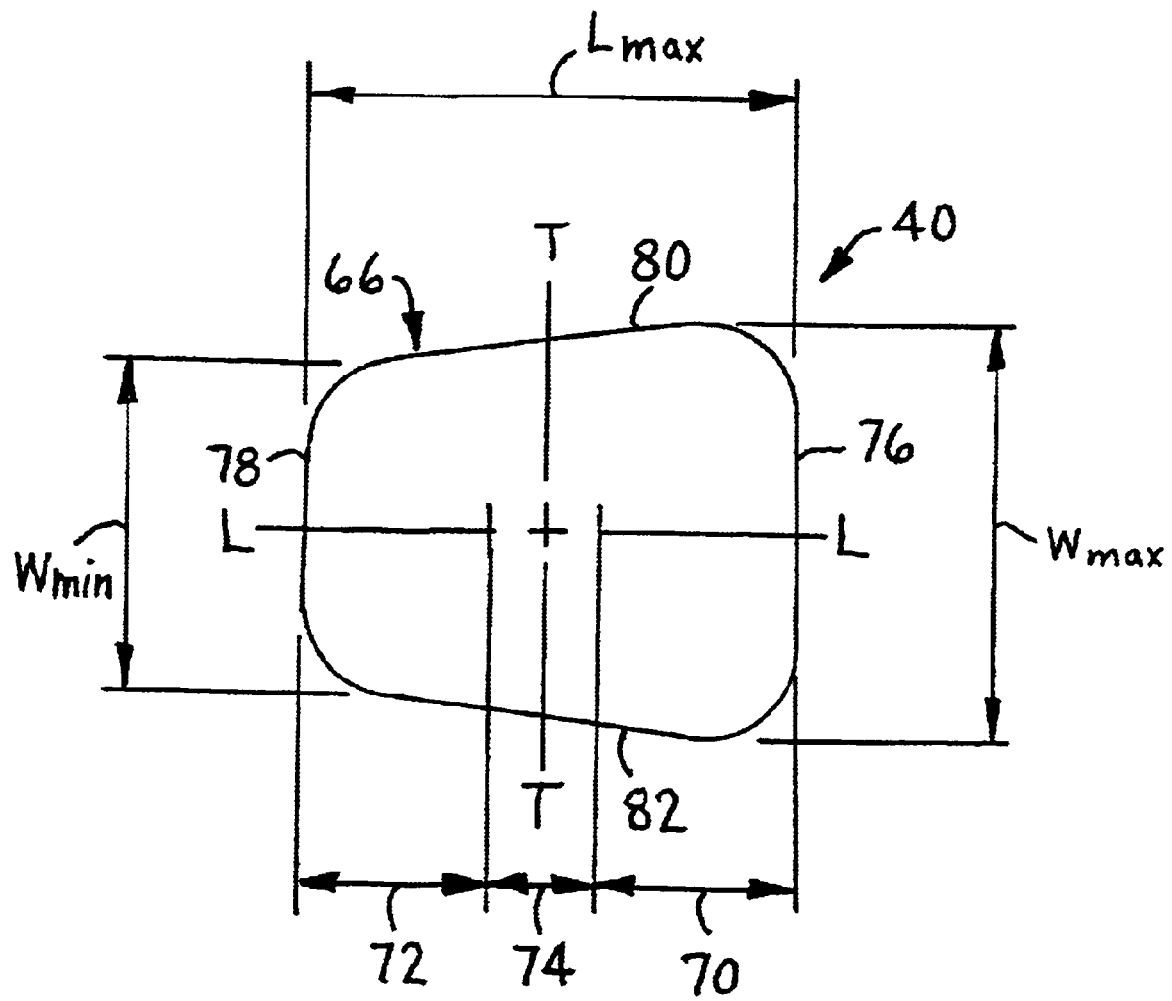
FIG. 6 is a top view illustrating a version of an absorbent article similar to that illustrated in FIG. 3.
Figure 7:
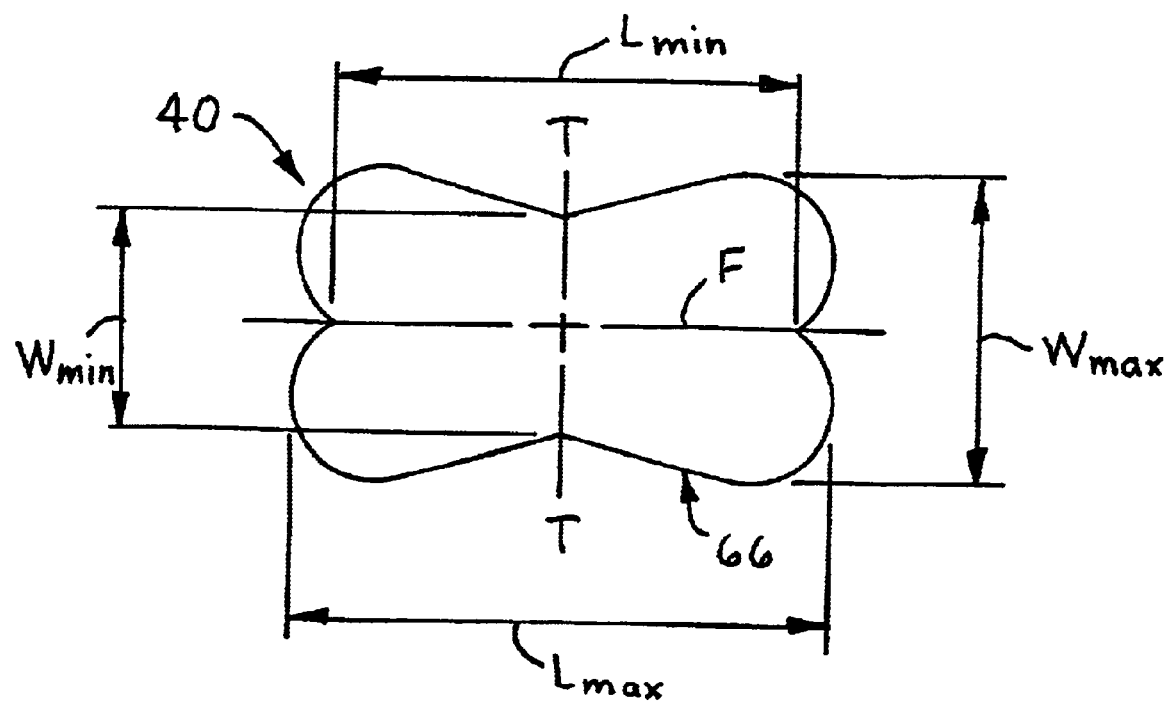
FIG. 7 is a top view illustrating an alternate version of an absorbent article.
Figure 8:
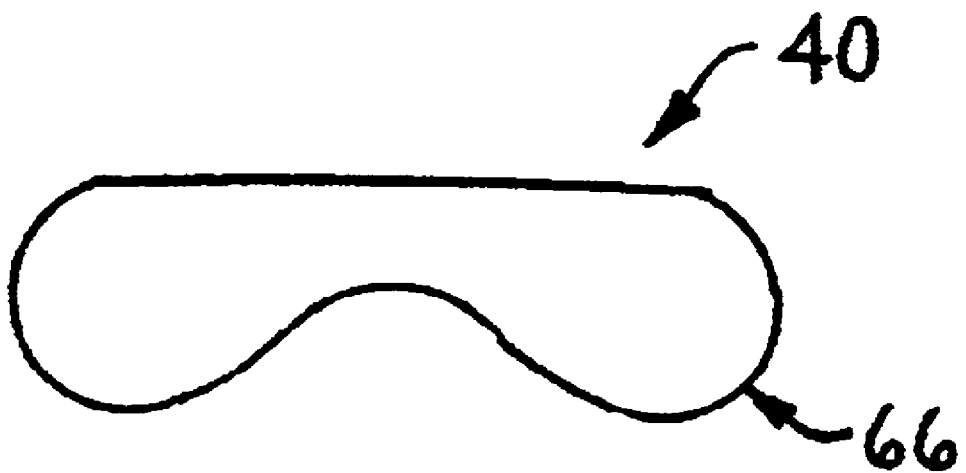
FIG. 8 is a cross-sectional view illustrating another alternate version of an absorbent article.

Turning now to FIG. 5, an absorbent article (40) is illustrated as including a fluid permeable cover (62), a liquid impermeable baffle (64) and an absorbent (66) situated between the cover and the baffle. As illustrated in FIG. 6, the absorbent (66) has a first end region (70), a second end region (72), and a central region (74) disposed between each end region. The absorbent article (40) should be of a suitable size and shape that allows at least a portion of the absorbent article to be disposed within the vestibule (42) of a female wearer. In addition, the absorbent article (40) desirably at least partially occludes and intercepts the flow of menstrual fluid, urine or other bodily exudates from the wearer's vaginal orifice (56) and/or urethral orifice (58).

The absorbent (66), and thus the absorbent article (40), generally displays a geometry extending between spaced apart first (76) and second (78) transverse end areas. The overall geometry is completed by noting that the absorbent (66), and thus the absorbent article (40), also includes spaced apart first (80) and second (82) longitudinal sides ranging between the transverse end areas (76, 78), these collectively sometimes being referred to herein as the perimetral sides (i.e., those defining the periphery).

The geometry of the absorbent (66) is a significant factor affecting the overall size and effectiveness of the absorbent article (40). In general, the absorbent (66) has a maximum width ($W_{max}$), measured along a line laying generally parallel to the principal transverse axis (T) and running from one longitudinal side to the opposing longitudinal side (80, 82), and a minimum width ($W_{min}$), measured along a line also laying generally parallel to the principal transverse axis (T) and running from one longitudinal side to the opposing longitudinal side (80, 82). The maximum width ($W_{max}$) of the absorbent (66) typically is no greater than about 30; alternatively, no greater than about 40; alternatively, no greater than about 50; alternatively, no greater than about 60; or alternatively, no greater than about 70 mm. The minimum width ($W_{mm}$) of the absorbent (66) typically is no less than about 30; alternatively, no less than about 20; alternatively, no less than about 10; or alternatively, no less than about 5 mm. Thus, the absorbent (66) may have a width ranging between no less than about 5 mm up to no greater than about 70 mm; although the approximate width(s) of the absorbent may vary according to, inter alia, the general design and intended disposition of the absorbent article (40) within the vestibule (42) of a female wearer. One of skill in the art will readily appreciate that certain versions of the absorbent (66), and thus certain versions of the absorbent article (40), may have a minimum width ($W_{mm}$) equal to its maximum width ($W_{max}$). In such instances, reference is generally made only to the maximum width ($W_{max}$).

The absorbent (66) also has a maximum length ($L_{max}$), measured along a line laying generally parallel to the principal longitudinal axis (L) and running from one transverse end area to the other transverse end area (76, 78). The maximum length ($L_{max}$) of the absorbent (66) typically is no greater than about 40; alternatively, no greater than about 50; alternatively, no greater than about 60; alternatively, no greater than about 70; alternatively, no greater than about 80; alternatively, no greater than about 90; or alternatively, no greater than about 100 mm. The absorbent (66) may also have a minimum length ($L_{min}$), measured along a line also laying generally parallel to the principal longitudinal axis (L) and running from one transverse end area to the other transverse end area (76, 78). The minimum length ($L_{mm}$) of the absorbent (66) typically is no less than about 100; alternatively, no less than about 90; alternatively, no less than about 80; alternatively, no less than about 70; alternatively, no less than about 60; alternatively, no less than about 50; or alternatively, no less than about 40 mm. Thus, the absorbent (66) may have a length ranging between no less than about 40 mm up to no greater than about 100 mm; although the approximate length(s) of the absorbent may vary according to, inter alia, the general design and intended disposition of the absorbent article (40) within the vestibule (42) of a female wearer. One of skill in the art will readily appreciate that certain versions of the absorbent (66), and thus certain versions of the absorbent article (40), may have a minimum length ($L_{min}$) equal to its maximum length ($L_{max}$). In such instances, as illustrated at least in FIG. 6, reference is generally made only to the maximum length ($L_{max}$). A version of an absorbent (66), and thus a version of an absorbent article (40), having a maximum length ($L_{max}$) not equal to its minimum length ($L_{min}$) is illustrated at least in FIG. 7.

The first end region (70) and the second end region (72) each minimally extend outwardly from the central region (74) toward the transverse end areas (76 and 78, respectively) of the absorbent (66) a distance of no less than about 30; alternatively, no less than about 20; or alternatively, no less than about 10% of the maximum length ($L_{max}$) of the absorbent. The first end region (70) and the second end region (72) each maximally extend outwardly from the central region (74) toward the transverse end areas (76 and 78, respectively) of the absorbent (66) a distance of no greater than about 20; alternatively, no greater than about 30; or alternatively, no greater than about 40% of the maximum length ($L_{max}$) of the absorbent. Thus, the end regions (70, 72) may occupy from a minimum of about 20% up to a maximum of about 80% of the maximum length ($L_{max}$) of the absorbent (66); although the approximate size of the first and second end regions may vary according to, inter alia, the general design and intended disposition of the absorbent article (40) within the vestibule (42) of a female wearer.

The absorbent article (40) is desirably provided with sufficient capacity to absorb and retain the intended amount and type of bodily exudate(s). The absorbent capacity is provided by a fluid retentive core or absorbent generally identified as 66. For at least menstrual fluid, the absorbent (66) desirably has a minimum capacity of no less than about 19; alternatively, no less than about 18; alternatively, no less than about 17; alternatively, no less than about 16; alternatively, no less than about 15; alternatively, no less than about 14; alternatively, no less than about 13; alternatively, no less than about 12; alternatively, no less than about 11; alternatively, no less than about 10; alternatively, no less than about 9; alternatively, no less than about 8; alternatively, no less than about 7; alternatively, no less than about 6; alternatively, no less than about 5; alternatively, no less than about 4; alternatively, no less than about 3; alternatively, no less than about 2; or alternatively, no less than about 1 g/g. The absorbent (66) also may have a maximum capacity of no greater than about 5; alternatively, no greater than about 6; alternatively, no greater than about 7; alternatively, no greater than about 8; alternatively, no greater than about 9; alternatively, no greater than about 10; alternatively, no greater than about 11; alternatively, no greater than about 12; alternatively, no greater than about 13; alternatively, no greater than about 14; alternatively, no greater than about 15; alternatively, no greater than about 16; alternatively, no greater than about 17; alternatively, no greater than about 18; alternatively, no greater than about 19; alternatively, no greater than about 20; alternatively, no greater than about 25; or alternatively, no greater than about 30 g/g. Thus, the absorbent (66) may have an absorbent capacity ranging between no less than about 1 g/g up to no greater than about 30 g/g; although the approximate capacity of the absorbent may vary according to, inter alia, the general design and intended disposition of the absorbent article (40) within the vestibule (42) of a female wearer. One of skill in the art will readily realize that the addition of superabsorbent polymer(s) or coated superabsorbent polymer(s) to the absorbent (66) typically has the effect of substantially increasing the absorbent capacity.

Describing the individual elements in greater detail, the absorbent (66) has an upper or body-facing surface and a lower surface (or surface opposed to the upper or body-facing surface) and may include any material capable of absorbing and/or adsorbing and thereafter retaining the intended bodily exudate(s). Suitable materials are also generally hydrophilic, compressible and conformable. The absorbent (66) may be formed from any of the materials well known to those of ordinary skill in the art. Examples of such materials include, but are not limited to, various natural or synthetic fibers, multiple plies of creped cellulose wadding, fluffed cellulose fibers, rayon or other regenerated cellulose materials, wood pulp fibers or comminuted wood pulp fibers, airlaid material, textile fibers, a blend of polyester and polypropylene fibers, absorbent foams, absorbent sponges, superabsorbent polymers, coated superabsorbent polymers, fibrous bundles or nits, or any equivalent material or combination of materials. Also suitable for use would be hydrophobic material that has been rendered hydrophilic according to any of a number of known methods for so doing. The total absorbent capacity of the absorbent (66) should, however, be compatible with the design exudate loading and the intended use of the absorbent article (40). Further, the size and absorbent capacity of the absorbent (66) may be varied. Therefore, the dimension, shape, and configuration of the absorbent (66) may be varied (e.g., the absorbent may have a varying thickness as illustrated at least in FIGS. 8 and 9, or a hydrophilic gradient, or may contain superabsorbent polymer(s) and the like).

The absorbent (66) generally has a thickness, caliper or height (H), as illustrated at least in FIG. 4, measured along a line lying generally parallel to the z-axis. The minimum thickness of the absorbent (66) typically is no less than about 9; alternatively, no less than about 8; alternatively, no less than about 7; alternatively, no less than about 6; alternatively, no less than about 5; alternatively, no less than about 4; alternatively, no less than about 3; alternatively, no less than about 2; alternatively, no less than about 1; or alternatively, no less than about 0.5 mm. The maximum thickness of the absorbent (66) typically is no greater than about 2; alternatively, no greater than about 3; alternatively, no greater than about 4; alternatively, no greater than about 5; alternatively, no greater than about 6; alternatively, no greater than about 7; alternatively, no greater than about 8; alternatively, no greater than about 9; or alternatively, no greater than about 10 mm. Thus, the absorbent (66) may have a thickness of about 10 mm or less; although the approximate thickness of the absorbent may vary according to, inter alia, the general design and intended disposition of the absorbent article (40) within the vestibule (42) of a female wearer.

The absorbent (66) desirably also has a relatively low density which is deemed desirable for comfort. Generally, the absorbent has a density of less than about 0.5 g/cc. Stated differently, the absorbent (66) typically has a maximum density of no greater than about 0.5; alternatively, no greater than about 0.4; alternatively, no greater than about 0.3; alternatively, no greater than about 0.2; alternatively, no greater than about 0.1; alternatively, no greater than about 0.09; alternatively, no greater than about 0.08; alternatively, no greater than about 0.07; alternatively, no greater than about 0.06; alternatively, no greater than about 0.05; alternatively, no greater than about 0.04; alternatively, no greater than about 0.03; or alternatively, no greater than about 0.02 g/cc. The absorbent (66) generally also has a minimum density of typically no less than about 0.01; alternatively no less than about 0.02; alternatively, no less than about 0.03; alternatively, no less than about 0.04; alternatively, no less than about 0.05; alternatively, no less than about 0.06; alternatively, no less than about 0.07; alternatively, no less than about 0.08; alternatively, no less than about 0.09; alternatively, no less than about 0.1; alternatively, no less than about 0.2; alternatively, no less than about 0.3; or alternatively, no less than about 0.4 g/cc. Thus, the density of the absorbent (66) may range up to about 0.5 g/cc; although the approximate density of the absorbent may vary according to, inter alia, the general design and intended disposition of the absorbent article (40) within the vestibule (42) of a female wearer.

The absorbent (66) also desirably has a basis weight of less than about 600 grams per square meter (gsm). Stated differently, the absorbent (66) typically has a maximum basis weight of no greater than about 600; alternatively, no greater than about 500; alternatively, no greater than about 400; alternatively, no greater than about 300; alternatively, no greater than about 200; or alternatively, no greater than about 100 gsm. Generally, the absorbent (66) also has a minimum basis weight of typically no less than about 0.1; alternatively, no less than about 50; alternatively, no less than about 100; alternatively, no less than about 150; alternatively, no less than about 200; alternatively, no less than about 250; alternatively, no less than about 300; alternatively, no less than about 350; alternatively, no less than about 400; alternatively, no less than about 450; alternatively, no less than about 500; or alternatively, no less than about 550 gsm. Thus, the absorbent (66) may have a basis weight of about 600 gsm or less; although the approximate basis weight of the absorbent may vary according to, inter alia, the general design and intended disposition of the absorbent article (40) within the vestibule (42) of a female wearer. A specific example of a suitable absorbent would be similar to a coform material made of a blend of polypropylene and cellulose fibers and used in KOTEX® maxi pantiliners and obtainable from Kimberly-Clark Corporation, Neenah, Wis., USA.

The optional baffle (64) typically resides on the lower surface of the absorbent (66) and may be constructed from any desired material that is liquid-impermeable. Desirably, the baffle (64) will permit the passage of air and moisture vapor out of the absorbent (66), while blocking the passage of bodily fluid(s). An example of a suitable baffle material is a micro-embossed, polymeric film, such as polyethylene, polypropylene or polyester, having a minimum thickness of no less than about 0.025 mm and a maximum thickness of no greater than about 0.13 mm. Bicomponent films can also be used, as well as woven and nonwoven fabrics which have been treated to render them liquid-impermeable. An example of another suitable material is a closed cell polyolefin foam. A closed cell polyethylene foam may also work well.

The baffle (64) may be maintained in secured relation with the absorbent (66) by bonding all or a portion of the adjacent surfaces to one another. A variety of bonding methods known to one of skill in the art may be utilized to achieve any such secured relation. Examples of such methods include, but are not limited to, ultrasonics, thermal bonding, or the application of adhesives in a variety of patterns between the two adjoining surfaces. A specific example of a baffle material would be similar to a polyethylene film used on KOTEX® pantiliners and obtainable from Pliant Corporation, Schaumburg, Ill., USA.

The optional fluid permeable cover (62) has an upper surface and a lower surface, with the upper surface typically contacting the body of the wearer and receiving bodily exudate(s). The cover (62) desirably is made of a material that is flexible and non-irritating to the tissues within the vestibule (42) of a female wearer. As used herein, the term "flexible" is intended to refer to materials which are compliant and readily conform to the bodily surface(s) or respond by easily deforming in the presence of external forces.

The cover (62) is provided for comfort and conformability and functions to direct bodily exudate(s) away from the body and toward the absorbent (66). The cover (62) should retain little or no liquid in its structure so that it provides a relatively comfortable and non-irritating surface next to the tissues within the vestibule (42) of a female wearer. The cover (62) can be constructed of any woven or nonwoven material which is also easily penetrated by bodily fluids contacting its surface. Examples of suitable materials include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs and net material also work well. A specific example of a suitable cover material would be similar to a bonded carded web made of polypropylene and polyethylene used as a cover stock for KOTEX® pantiliners and obtainable from Sandler Corporation, Germany. Other examples of suitable materials are composite materials of a polymer and a non-woven fabric material. The composite materials are typically in the form of integral sheets generally formed by the extrusion of a polymer onto a web of spunbond material. The fluid permeable cover (62) can also contain a plurality of apertures (not shown) formed therein which are intended to increase the rate at which bodily fluid(s) can penetrate into the absorbent (66).

A physiologically hydrous cover material is also suitable for use. As used herein, the term "physiologically hydrous" is intended to connote a cover material which maintains a suitably moist interface between the tissues of the vestibule (42) and the absorbent article (40) when disposed in that vestibular environment; one that is benign respecting the requirements of comfort associated with the interposition of fabric or fabric-like structures within the moist tissue environment of the vestibule, keeping in mind as well the self-evident factor that the absorbent article is receiving bodily fluid(s) migrating through the vestibule and must conduct the same to the absorbent (66). Thus, while not "hydrous" in the classic sense prior to use (inasmuch as the cover will be dry at that time) the cover (62) maintains (or at least does not interfere with the maintenance of) the proper moisture level or balance required within the vestibule (42).

The cover (62) can also have at least a portion of the surface treated with a surfactant to render the cover more hydrophilic. This results in permitting the insulting bodily fluid(s) to more readily penetrate the cover (62). The surfactant may also diminish the likelihood that the insulting bodily fluid(s), such as menstrual fluid, will flow off the cover (62) rather than being absorbed by the absorbent (66). One suitable approach provides for the surfactant to be substantially evenly distributed across at least a portion of the upper surface of the cover (62) that overlays the upper surface of the absorbent (66).

The cover (62) may be maintained in secured relation with the absorbent (66) by bonding all or a portion of the adjacent surfaces to one another. A variety of bonding methods known to one of skill in the art may be utilized to achieve any such secured relation. Examples of such methods include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

The cover (62) typically resides on the upper surface of the absorbent (66), but alternatively can surround and partially or entirely enclose the absorbent. Alternatively, the cover (62) and the baffle (64) can have peripheries which extend outward beyond the periphery of the absorbent (66) and can be peripherally joined together to form an edge (84), as illustrated at least in FIG. 5. Utilizing known techniques, such as, for example, gluing, crimping, hot-sealing or the like, the edge (84) may be formed either entirely, so that the entire periphery of the absorbent (66) is circumscribed by their joinder, or the cover (62) and the baffle (64) can be partially peripherally joined. To minimize the possibility of irritation and/or discomfort to the wearer of the absorbent article (40), it is desired that the edge (84) and at least the area of the absorbent article immediately adjacent the edge be soft, compressible and conformable. Desirably, any edge (84) so formed shall have a width no greater than about 10; alternatively, no greater than about 9; alternatively, no greater than about 8; alternatively, no greater than about 7; alternatively, no greater than about 6; alternatively, no greater than about 5; alternatively, no greater than about 4; alternatively, no greater than about 3; alternatively, no greater than about 2; or alternatively, no greater than about 1 mm. In addition, any edge (84) so formed shall desirably have a width of no less than about 0.5; alternatively, no less than about 1; alternatively, no less than about 2; alternatively, no less than about 3; alternatively, no less than about 4; alternatively, no less than about 5; alternatively, no less than about 6; alternatively, no less than about 7; alternatively, no less than about 8; or alternatively, no less than about 9 mm. Thus, any edge (84) so formed may have a width ranging from no less than about 0.5 mm up to no greater than about 10 mm; although the approximate width of any edge may vary according to, inter alia, the general design and intended disposition of the absorbent article (40) within the vestibule (42) of a female wearer. In other versions, the cover (62) and/or the baffle (64) can have a periphery that is coterminous with the periphery of the absorbent (66).

Positioned either on or substantially parallel to the principal longitudinal axis (L) of the absorbent (66), is, optionally, a desired axis of flexure (F). A desired axis of flexure (F) generally runs in the longitudinal direction, i.e., along the x direction, and may be off center from the principal longitudinal axis (L) a distance of no greater than about 10; alternatively, no greater than about 9; alternatively, no greater than about 8; alternatively, no greater than about 7; alternatively, no greater than about 6; alternatively, no greater than about 5; alternatively, no greater than about 4; alternatively, no greater than about 3; alternatively, no greater than about 2; or alternatively, no greater than about 1 mm. Desirably, a desired axis of flexure (F) is aligned along the principal longitudinal axis (L). A desired axis of flexure (F) typically minimally extends longitudinally no less than about 90; alternatively, no less than about 80; alternatively, no less than about 70; alternatively, no less than about 60; alternatively, no less than about 50; or alternatively, no less than about 40% of the maximum length ($L_{max}$) of the absorbent (66). A desired axis of flexure (F) typically extends longitudinally no greater than about 50; alternatively, no greater than about 60; alternatively, no greater than about 70; alternatively, no greater than about 80; alternatively, no greater than about 90; or alternatively, no greater than about 100% of the maximum length ($L_{max}$) of the absorbent (66). A desired axis of flexure (F) may result naturally from the dimensions, shape, and/or configuration of the absorbent (66), or the absorbent may be imparted with a weakened axis or region to create a desired axis of flexure. A desired axis of flexure (F) may also be formed by any of the techniques known to one of skill in the art, including, for example, scoring, pre-folding, slitting, embossing, or the like. Although a desired axis of flexure (F) is described herein as residing in the absorbent (66), one of skill in the art will readily appreciate that a desired axis of flexure may be formed in either the cover (62), the baffle (64) and/or the absorbent; the cover and the baffle; the cover and the absorbent; or the baffle and the absorbent. When present, a desired axis of flexure (F) typically allows an absorbent article (40) to be folded more easily prior to disposition within the vestibule (42) of a female wearer.

The absorbent article (40) also has a thickness, caliper or height (H), as illustrated at least in FIGS. 4 and 5, measured along a line laying generally parallel to the z-axis. The minimum thickness of the absorbent article (40) typically is no less than about 9; alternatively, no less than about 8; alternatively, no less than about 7; alternatively, no less than about 6; alternatively, no less than about 5; alternatively, no less than about 4; alternatively, no less than about 3; alternatively, no less than about 2; alternatively, no less than about 1; or alternatively, no less than about 0.5 mm. The maximum thickness of the absorbent article (40) typically is no greater than about 1; alternatively, no greater than about 2; alternatively, no greater than about 3; alternatively, no greater than about 4; alternatively, no greater than about 5; alternatively, no greater than about 6; alternatively, no greater than about 7; alternatively, no greater than about 8; alternatively, no greater than about 9; or alternatively, no greater than about 10 mm. Thus, the absorbent article (40) may have a thickness of about 10 mm or less; although the approximate thickness of the absorbent article may vary according to, inter alia, the general design and intended disposition of the absorbent article within the vestibule (42) of a female wearer.

Figure 9:
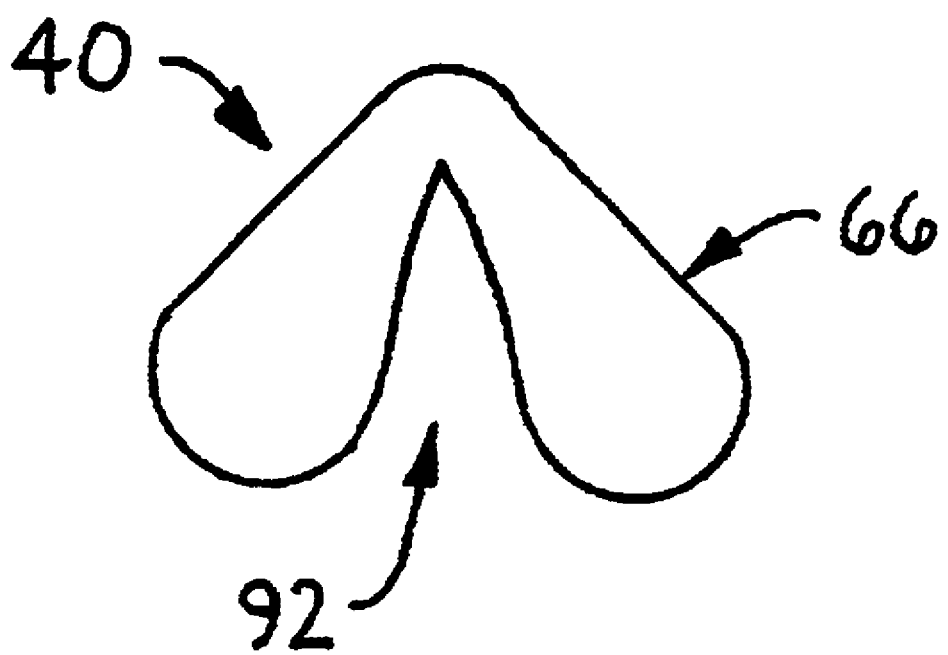
FIG. 9 is a cross-sectional view illustrating the version of FIG. 8 in a substantially folded position.
Figure 10:
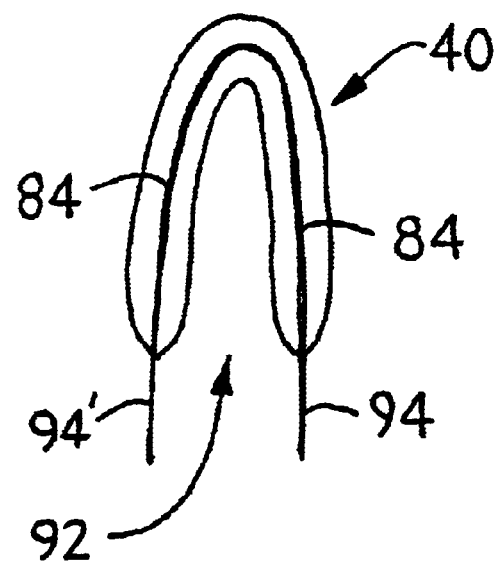
FIG. 10 illustrates an enlarged view of a version of an absorbent article folded substantially about a principal axis.
Figure 11:
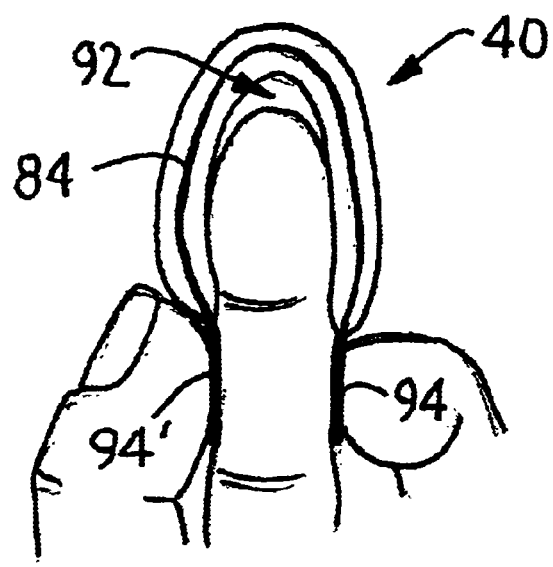
FIG. 11 illustrates an exaggerated enlarged view of a version of an absorbent article folded substantially about a principal axis and being grasped for disposition in the vestibule by the wearer's fingers.
Figure 12:
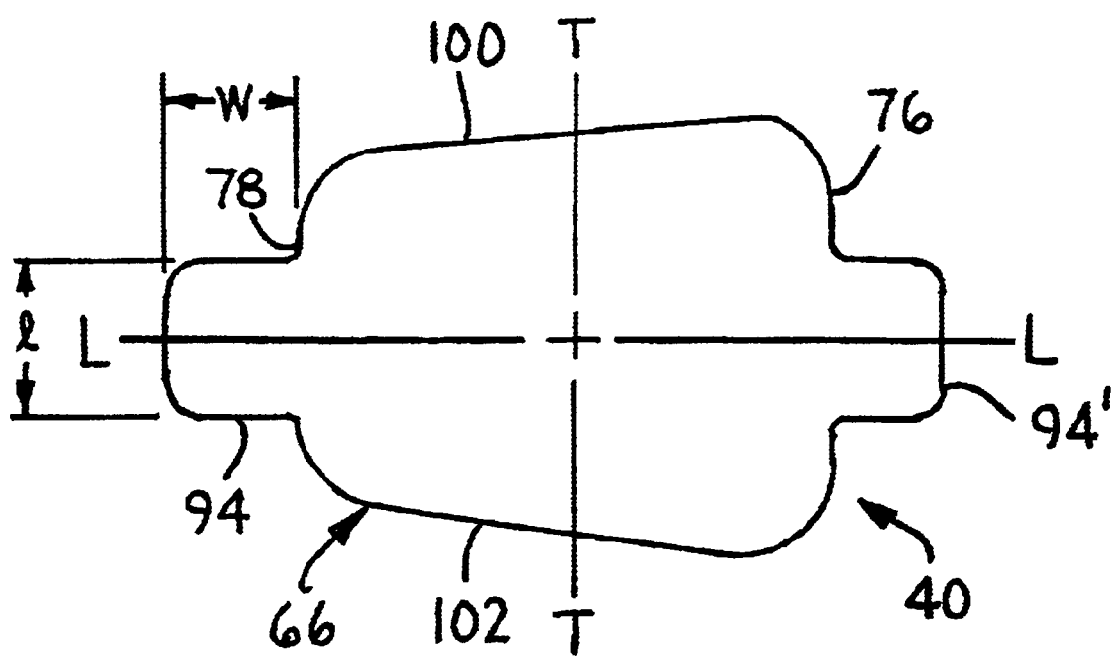
FIG. 12 illustrates an alternate version of an absorbent article having a tab extending outward from each transverse end area.
Figure 13:
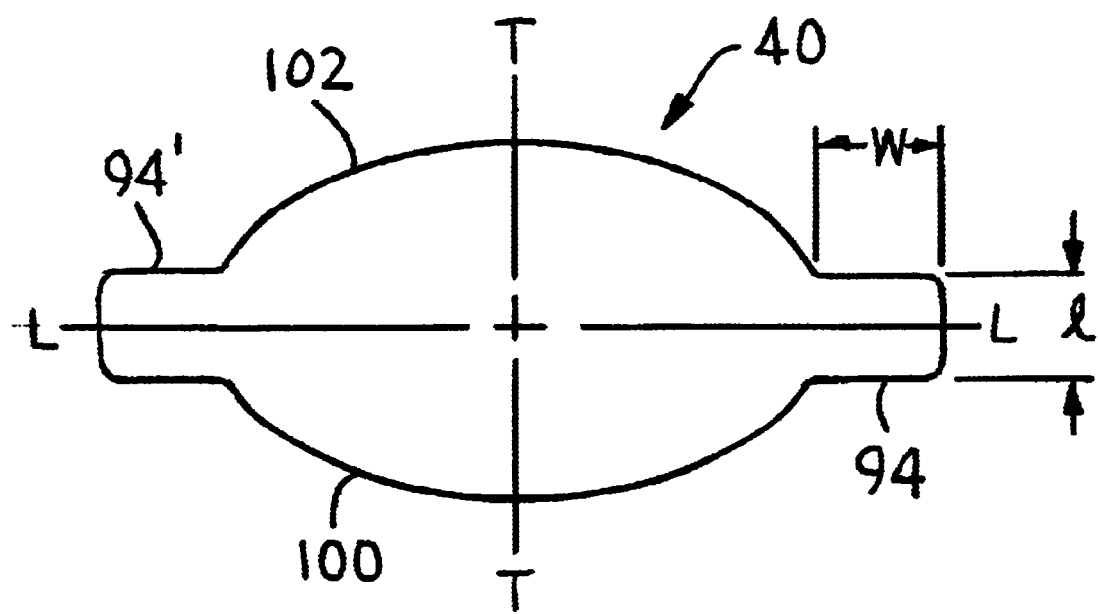
FIG. 13 illustrates a further version of an absorbent article having a tab extending outward from each transverse end area.

The absorbent article (40) typically is folded along an axis lying on or positioned parallel to the principal longitudinal axis (L), as illustrated at least in FIGS. 9, 10 and 11, prior to disposition within the vestibule (42) of the female wearer. When folded along such an axis, the absorbent article (40) will form a recess (92) which protects the wearer's finger(s) from soiling when the absorbent article is disposed within the vestibule (42). Once inserted, the absorbent article (40) may have a tendency to unfold in an attempt to fill the vestibule and thus maintain the upper surface of the absorbent article in contact with the tissues of the vestibule (42). The absorbent article (40) may be resiliently biased along the axis about which it is folded to increase the tendency of the absorbent article to unfold. Alternatively, the absorbent (66) of the absorbent article (40) may be thicker along its longitudinal edges, as illustrated at least in FIGS. 8 and 9, thus also demonstrating a biasing effect, if desired, which is typically intended to allow the upper surface of the absorbent article (40) to contact the tissues of the vestibule (42). An absorbent article (40) as described herein, however, does not necessarily require any additional features to maintain contact with the tissues of the vestibule (42) of the female wearer. The naturally moist surfaces of the tissues of the vestibule (42) typically demonstrate a tendency to maintain contact with the upper surface of the absorbent article (40).

As noted above, the wearer may fold the absorbent article (40) along an axis lying on or positioned parallel to the principal longitudinal axis (L) prior to disposition within the vestibule (42). The wearer may, therefore, hold the folded absorbent article (40) near the longitudinal sides as illustrated at least in FIG. 11. The absorbent article (40) may then be disposed within the vestibule (42) by the wearer exerting a force with a finger or fingers positioned in the recess (92) formed by the folded absorbent article.

Although previously described herein as typically being folded along an axis lying on or positioned parallel to the principal longitudinal axis, an absorbent article (40) may also be folded along an axis lying on or positioned parallel to the principal transverse axis (T) prior to disposition within the vestibule (42) of the female wearer. When folded along such an axis, the absorbent article (40) typically still forms a recess (92) which protects the wearer's finger(s) from soiling when the absorbent article is disposed within the vestibule (42). Once inserted, the absorbent article (40) may have a tendency to unfold in an attempt to fill the vestibule and thus maintain the upper surface of the absorbent article in contact with the tissues of the vestibule (42). The absorbent article (40) may be resiliently biased along the axis about which it is folded to increase the tendency of the absorbent article to unfold. Alternatively, the absorbent (66) of the absorbent article (40) may be thicker along its transverse end areas (76, 78) thus also demonstrating a biasing effect, if desired, which is typically intended to allow the upper surface of the absorbent article (40) to contact the tissues of the vestibule (42). An absorbent article (40) as described herein, however, does not necessarily require any additional features to maintain contact with the tissues of the vestibule (42) of the female wearer. The naturally moist surfaces of the tissues of the vestibule (42) typically demonstrate a tendency to maintain contact with the upper surface of the absorbent article (40).

Suitable for use with certain versions of the absorbent articles described herein would be at least one placement and removal tab (94) extending outward from the periphery of at least one transverse end area (76, 78) of an absorbent article (40). While one such tab (94) is theorized as working effectively in the placement and removal of an absorbent article (40) such as a labial pad, it is believed that at least two tabs (94 and 94'), i.e., one tab extending from the periphery of each transverse end area (76, 78) of the absorbent article, are also effective in the placement and removal of an absorbent article. Consequently, in the discussion that follows, unless otherwise noted, the absorbent article (40) will have at least two tabs (94, 94'). While it is not necessary that the tabs (94, 94') be identical, or, more properly, mirror images one of the other, they desirably are. Thus the description of the first will be a description of any other tab. Discussion of any other tab will, therefore, be omitted for clarity of exposition. Corresponding elements are indicated in the drawings by reference numerals and primed reference numerals. In addition, although illustrated with certain versions of the absorbent article (40) disclosed herein, it will be understood that the tabs (94, 94') herein may be incorporated into a number of other suitably shaped and dimensioned labial pads. Such suitable shapes and dimensions include, but are not limited to, rectangular, ovoid-like, elliptical, trapezoidal, circular-like, triangular, square-shaped, teardrop-like, diamond-shaped, butterfly, pear-shaped, heart-shaped or a variety of combinations thereof.

Extending outward from the periphery of a transverse end area (76, 78) of an absorbent article (40), the tab (94) can be of any suitable configuration. Non-limiting examples of shapes for the tab (94) include, ovoid, elliptical, trapezpoidal, rectangular, triangular, diamond-shaped, circular, semi-circular, or any combination of the above. The tab (94) may be integrally formed with the absorbent article (40) or it may be a separate element joined to the absorbent article. One of skill in the art will readily appreciate that when the tab (94) is a separate element joined to the absorbent article (40), the tab may be so joined by a number of known methods including melt fusion, adhesion, or other joining means. The phrase "integrally formed" is intended to indicate that the tab (94) is not joined to the absorbent article (40), but rather is an extension of: the cover (62), the baffle (64), and/or the absorbent (66); the cover and the baffle; the cover and the absorbent; or the baffle and the absorbent.

The tab (94) has a length (l), measured along a line laying generally parallel to the principal transverse axis (T) of an absorbent article (40), and a width (w), measured along a line laying generally parallel to the principal longitudinal axis (L) of an absorbent article. The tab (94) has sufficient dimensions to aid the female user in disposition of the absorbent article (40) within the vestibule (42) and, optionally, removal of the absorbent article from the vestibule. The phrase "sufficient dimensions" is intended to indicate that the tab (94) can be grasped between the index finger and the thumb or, if there are, for example, two tabs, between the index finger and the thumb and the middle finger and the index finger. Typically, the length (l) of the tab (94) is no greater than the maximum width ($W_{max}$) of the absorbent (66). More specifically, the length (l) of the tab (94) typically is no greater than about 70; alternatively, no greater than about 60; alternatively, no greater than about 50; alternatively, no greater than about 40; alternatively, no greater than about 30; alternatively, no greater than about 20; alternatively, no greater than about 10; or alternatively, no greater than about 5 mm. Stated differently, the length (l) of the tab (94) is typically no greater than about 100; alternatively, no greater than about 90; alternatively, no greater than about 80; alternatively, no greater than about 70; alternatively, no greater than about 60; alternatively, no greater than about 50; alternatively, no greater than about 40; alternatively, no greater than about 30; alternatively, no greater than about 20; or alternatively, no greater than about 10% of the maximum width ($W_{max}$) of the absorbent (66). The length (l) of the tab (94) typically is no less than about 1; alternatively, no less than about 5; alternatively, no less than about 10; alternatively, no less than about 20; alternatively, no less than about 30; alternatively, no less than about 40; alternatively, no less than about 50; or alternatively, no less than about 60 mm. One of skill in the art will readily appreciate that the length (l) of the tab (94) may vary according to, inter alia, the general design and intended disposition of the absorbent article within the vestibule (42) of a female user.

In addition to having a length (l), the tab (94) also has a width (w). The width (w) of the tab (94) typically is no greater than about 50; alternatively, no greater than about 40; alternatively, no greater than about 30; alternatively, no greater than about 20; alternatively, no greater than about 10; alternatively, no greater than about 7.5; alternatively, no greater than about 5; alternatively, no greater than about 2.5; or alternatively, no greater than about 1 mm. The width (w) of the tab (94) typically is no less than about 1; alternatively, no less than about 2.5; alternatively, no less than about 5; alternatively, no less than about 7.5; alternatively, no less than about 10; alternatively, no less than about 20; alternatively, no less than about 30; or alternatively, no less than about 40 mm. One of skill in the art will readily appreciate that the width (w) of the tab (94) may vary according to, inter alia, the general design and intended disposition of the absorbent article within the vestibule (42) of a female user.

The dimensions of the tab (94) are limited only by the stress-strain properties of the tab material(s). Desirably any material used in the tabs (94, 94') is soft, compressible and conformable and thus similar to the material used in the fluid permeable cover (62), the liquid impermeable baffle (64) and/or the absorbent (66). Any such material desirably minimizes the possibility of irritation and/or discomfort to the wearer of the absorbent article (40).

The tab (94) of the present invention may be positioned in a variety of locations along the periphery of a transverse end area (76, 78) of an absorbent article (40). Generally, when a tab (94) extends outward from the periphery of a transverse end area (76, 78) of an absorbent article (40), any second tab (94') typically extends outward from the periphery of the opposing transverse end area (76, 78). The tabs (94, 94') as described herein offer a female wearer the opportunity to grasp the tabs to aid in the disposition of a labial pad into the vestibule. In addition, the tabs (94, 94') also offer a female wearer the opportunity to grasp the tabs to aid in the removal of a labial pad and thus minimize the likelihood that the female wearer's finger(s) will come into contact with the body-facing surface of the possibly soiled labial pad.

Figure 14:
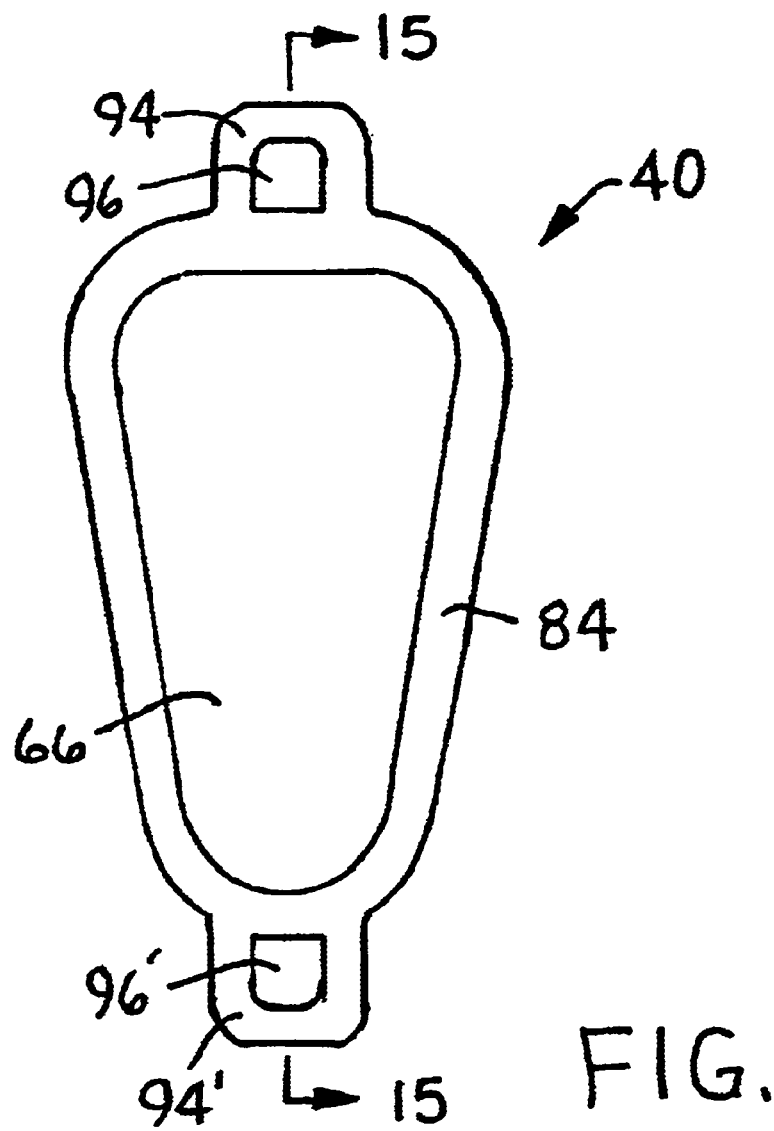
FIG. 14 illustrates yet a further version of an absorbent article having a tab extending outward from each transverse end area.
Figure 15:
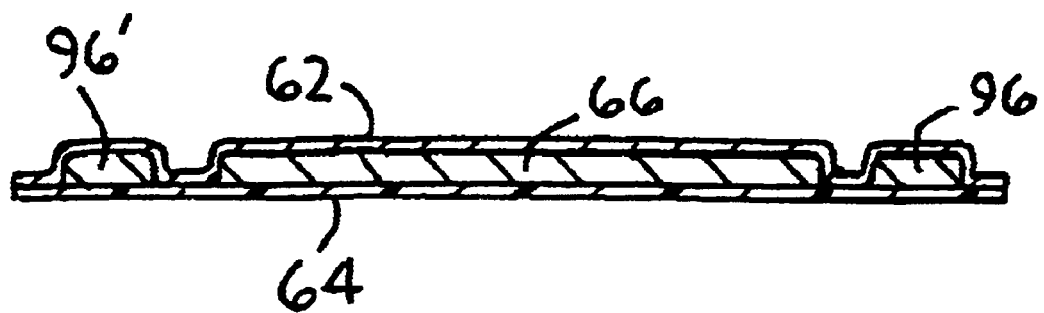
FIG. 15 illustrates a cross-sectional view of the absorbent article of FIG. 14 taken along line 15—15.

FIG. 14 illustrates an absorbent article (40) having at least one tab (94, 94') positioned along the periphery of each transverse end area (76, 78). Each tab (94, 94') has an integrally formed cover (62) and baffle (64). While the cover (62) and baffle (64) in FIG. 14 are integrally formed, each tab (94, 94') has a tab absorbent (96, 96') that is not integrally formed with the absorbent (66). Generally, the material of the tab absorbent (96, 96') is similar to the material of the absorbent (66). The presence of absorbent material in a tab typically increases the absorbent capacity of the absorbent article. FIG. 15 is a cross-sectional view of the absorbent (40) article of FIG. 14 taken along line 15—15.

Figure 16:
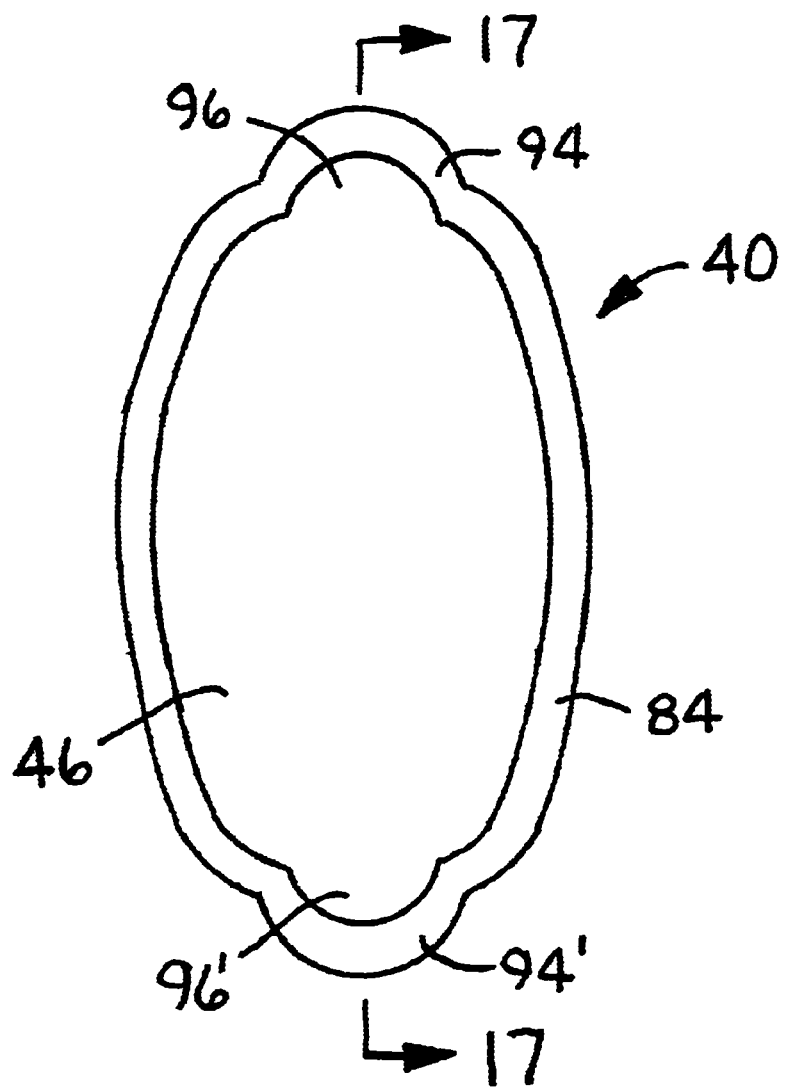
FIG. 16 illustrates yet another further version of an absorbent article having a tab extending outward from each transverse end area.
Figure 17:
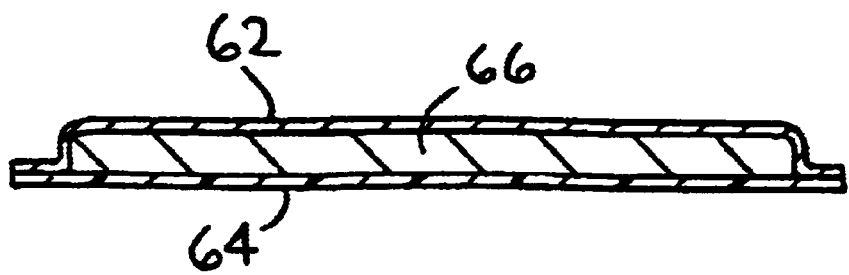
FIG. 17 illustrates a cross-sectional view of the absorbent article of FIG. 16 taken along line 17—17.

FIG. 16 illustrates an absorbent article (40) having at least one tab (94, 94') positioned along the periphery of each transverse end area (76, 78). Each tab (94, 94') has an integrally formed cover (62), baffle (64) and absorbent (66); however, for purposes of description, the absorbent extending outward of the periphery of a transverse end area (76, 78) is referred to as the tab absorbent (96, 96'). FIG. 17 is a cross-sectional view of the absorbent article (40) of FIG. 16 taken along line 17—17.

Figure 18:
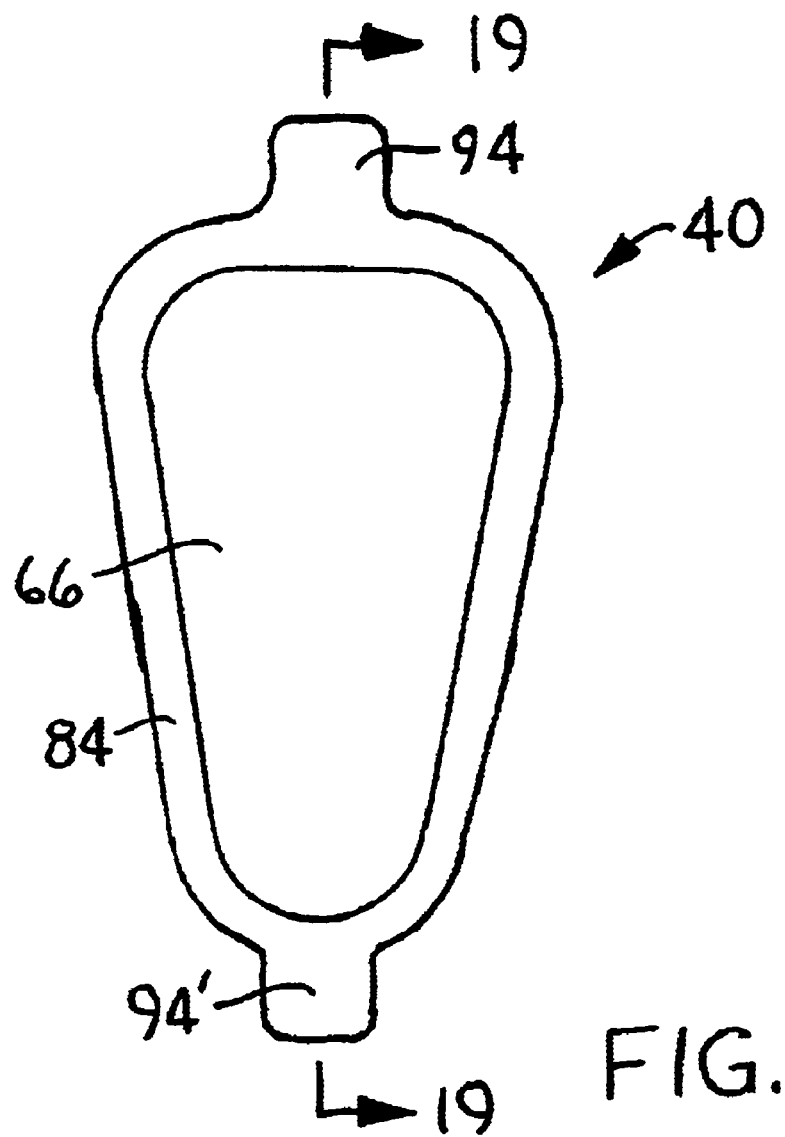
FIG. 18 illustrates still another a version of an absorbent article having a tab extending outward from each transverse end area.
Figure 19:
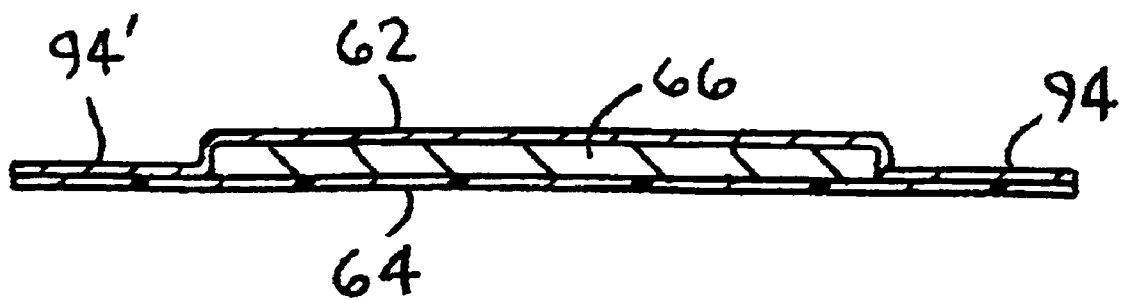
FIG. 19 illustrates a cross-sectional view of the absorbent article of FIG. 18 taken along line 19—19.

FIG. 18 illustrates an absorbent article (40) having one tab (94, 94') positioned along the periphery of each transverse end area (76, 78). Each tab (94, 94') has an integrally formed cover (63) and baffle (64). FIG. 19 is a cross-sectional view of the absorbent article (40) of FIG. 18 taken along line 19—19.

Although various versions or embodiments of the present invention have been disclosed and described in considerable detail, other embodiments are possible. Consequently, the spirit and scope of the appended claims should not be limited to the illustration and description of the various embodiments contained herein.

What is claimed is:

1. An absorbent article (40) comprising a fluid permeable cover (62), a liquid impermeable baffle (64) and an absorbent (66) situated between the cover and the baffle, the absorbent article being configured to provide a labial pad for disposition within the vestibule of a female wearer, the absorbent article further comprising a principal longitudinal axis, a principal transverse axis, a body-facing surface, a surface opposed to the body-facing surface, a length, a width, a thickness, first (76) and second (78) longitudinally spaced apart transverse end areas, first (80) and second (82) spaced apart longitudinal sides, the longitudinal sides ranging between the transverse end areas and collectively defining a periphery of the absorbent article, and at least one tab (94) extending outward from the periphery of each of said first and second transverse end areas (76, 78); wherein said article is shorter along its principal transverse axis than along its principal longitudinal axis;

said article is configured to be folded along an axis positioned parallel to said principal transverse axis prior to disposition within the vestibule of the female wearer, the folding providing a recess that protects the wearer's finger(s) from soiling when the article is disposed in the vestibule;

said absorbent (66) has a maximum width ($W_{max}$) which is no greater than about 70 mm;

said absorbent (66) has a maximum length ($L_{max}$) which is no greater than about 100 mm;

each said tab (94) has a length (l) which is no greater than about 70 mm, and no greater than about 100% of the maximum width ($W_{max}$) of the absorbent (66);

each said tab (94) has a width (w) which is no greater than about 50 mm; and each said tab thereby has sufficient dimensions to allow a user to grasp the tabs and fold said article along the principal transverse axis prior to disposition within the vestibule of the female wearer.

2. The absorbent article of claim 1, wherein the tab comprises a fluid permeable material.

3. The absorbent article of claim 1, wherein the fluid permeable cover extends outward from the periphery of at least one transverse end area to form the tab.

4. The absorbent article of claim 1, wherein the tab comprises an absorbent material.

5. The absorbent article of claim 4, wherein the absorbent material of the tab further comprises a superabsorbent polymer.

6. The absorbent article of claim 1, wherein the absorbent extends outward from the periphery of at least one transverse end area to form the tab.

7. The absorbent article of claim 6, wherein the absorbent further comprises a superabsorbent polymer.

8. The absorbent article of claim 1, wherein the tab comprises a liquid impermeable material.

9. The absorbent article of claim 1, wherein the liquid Impermeable baffle extends outward from the periphery of at least one transverse end area to form the tab.

10. The absorbent article of claim 1, wherein the absorbent further comprises a superabsorbent polymer.

11. An absorbent article (40) comprising a liquid impermeable baffle (64) and an absorbent (66), the absorbent article being configured for disposition within the vestibule of a female wearer, the absorbent article further comprising a principal longitudinal axis, a principal transverse axis, a body-facing surface, a surface opposed to the body-facing surface, a length, a width, a thickness, first (76) and second (78) longitudinally spaced apart transverse end areas, first (80) and second (82) spaced apart longitudinal sides, the longitudinal sides ranging between the transverse end areas and collectively defining a periphery of the absorbent article, and at least one tab (94) extending outward from the periphery of each of said first and second transverse end areas (76, 78); wherein said article is shorter along its principal transverse axis than along its principal longitudinal axis;

said article is configured to be folded along an axis positioned parallel to said principal transverse axis prior to disposition within the vestibule of the female wearer, the folding providing a recess that protects the wearer's finger(s) from soiling when the article is disposed in the vestibule;

said absorbent (66) has a maximum width ($W_{max}$) which is no greater than about 70 mm;

said absorbent (66) has a maximum length ($L_{max}$) which is no greater than about 100 mm;

each said tab (94) has a length l) which is no greater than about 70 mm, and no greater than about 100% of the maximum width ($W_{max}$) of the absorbent (66);

each said tab (94) has a width (W) which is no greater than about 50 mm; and each said tab thereby has sufficient dimensions to allow a user to grasp the tabs and told said article along the axis positioned parallel to said principal transverse axis prior to disposition within the vestibule of the female wearer.

12. The absorbent article of claim 11, wherein the tab comprises a fluid permeable material.

13. The absorbent article of claim 11, wherein the absorbent article further comprises a fluid permeable cover (62).

14. The absorbent article of claim 13, wherein the fluid permeable cover extends outward from the periphery at least one transverse end area to form the tab.

15. The absorbent article of claim 11, wherein the tab comprises an absorbent material.

16. The absorbent article of claim 15, wherein the absorbent material of the tab further comprises a superabsorbent polymer.

17. The absorbent article of claim 11, wherein the absorbent extends outward from the periphery of at least one transverse end area to form the tab.

18. The absorbent article of claim 17, wherein the absorbent further comprises a superabsorbent polymer.

19. The absorbent article of claim 11, wherein the tab comprises a liquid impermeable material.

20. The absorbent article of claim 11, wherein the liquid impermeable baffle extends outward from the periphery of at least one transverse end area to form the tab.

21. The absorbent article at claim 11, wherein the absorbent further comprises a superabsorbent polymer.

22. An absorbent article (40) comprising an absorbent (66), the absorbent article being configured for disposition within the vestibule of a female wearer, the absorbent article further having a principal longitudinal axis, a principal transverse axis, a body-facing surface, a surface opposed to the body-facing surface, a length, a width, a thickness, first (76) and second (78) longitudinally spaced apart transverse end areas, first (80) and second (82) spaced apart longitudinal sides, the longitudinal sides ranging between the transverse end areas and collectively defining a periphery of the absorbent article, and at least one tab (94) extending outward from the periphery each of said first and second transverse end areas (76, 78); wherein said article is shorter along its principal transverse axis than along its principal longitudinal axis;

said article is configured to be folded along an axis positioned parallel to said principal transverse axis prior to disposition within the vestibule of the female wearer, the folding providing a recess that protects the wearer's finger(s) from soiling when the article is disposed in the vestibule;

said absorbent (66) has a maximum width ($W_{max}$) which is no greater than about 70 mm;

said absorbent (66) has a maximum length ($L_{max}$) which is no greater than about 100 mm;

each said tab (94) has a length (l) which is no greater than about 70 mm, and no greater than about 100% of the maximum width ($W_{max}$) of the absorbent (66);

each said tab (94) has a width (w) which is no greater than about 50 mm; and each said tab thereby has sufficient dimensions to allow a user to grasp the tabs and fold said article along the axis positioned parallel to said principal transverse axis prior to disposition within the vestibule of the female wearer.

23. The absorbent article of claim 22, wherein the tab comprises a fluid permeable material.

24. The absorbent article of claim 22, wherein the absorbent further comprises a fluid permeable cover (62).

25. The absorbent article of claim 24, wherein the fluid permeable cover extends outward from the periphery of at least one transverse end area to form the tab.

26. The absorbent article of claim 22, wherein the tab comprises an absorbent material.

27. The absorbent article of claim 26, wherein the absorbent material of the tab further comprises a superabsorbent polymer.

28. The absorbent article of claim 22, wherein the absorbent extends outward from the periphery of at least one transverse end area to form the tab.

29. The absorbent article of claim 28, wherein the absorbent further comprises a superabsorbent polymer.

30. The absorbent article of claim 22, wherein the tab comprises a liquid impermeable material.

31. The absorbent article of claim 22, wherein the absorbent article further comprises a liquid impermeable baffle (64).

32. The absorbent article of claim 31, wherein the liquid impermeable baffle extends outward from the periphery of at least one transverse end area to form the tab.

33. The absorbent article of claim 22, wherein the absorbent further comprises a superabsorbent polymer.

* * * * *